United States Patent [19]

Spraker

[11] 4,288,545

[45] Sep. 8, 1981

[54] MICROBIOLOGICAL PROCESS FOR REMOVING OLEAGINOUS MATERIAL FROM WASTEWATER AND MICROBIOLOGICAL COMBINATION CAPABLE OF SAME

[75] Inventor: Philip W. Spraker, Troutville, Va.

[73] Assignee: Sybron Corporation, Rochester, N.Y.

[21] Appl. No.: 4,241

[22] Filed: Jan. 17, 1979

[51] Int. Cl.³ ............................................. G12P 39/00
[52] U.S. Cl. ..................... 435/42; 435/253; 435/267; 435/833; 435/834; 435/835; 435/836; 435/837; 435/839; 435/875; 435/877; 210/601; 210/620; 210/632
[58] Field of Search ............... 435/834, 839, 836, 134, 435/253, 170, 172, 267, 262, 832, 281, 875, 877, 874, 42, 876, 248, 271, 837, 833, 835; 210/2, 11, 15, 17; 610/622, 620, 601

[56] References Cited

U.S. PATENT DOCUMENTS

| | | | |
|---|---|---|---|
| 3,025,151 | 3/1962 | Berg | 210/15 |
| 3,152,983 | 10/1964 | Davis et al. | 210/15 X |
| 3,878,303 | 4/1975 | Hashimoto | 210/15 X |

Primary Examiner—R. B. Penland
Attorney, Agent, or Firm—Sughrue, Mion, Zinn, Macpeak and Seas

[57] ABSTRACT

A process for removing oleaginous materials containing those of animal origin from wastewater comprising treating wastewater containing oleaginous material with a microbial combination of:

(a) a microorganism of the strain *Pseudomonas aeruginosa* mutant $SGRR_2$; and (b) at least one of:
  (i) a microorganism of the genus Bacillus; and
  (ii) a microorganism of the genus Pseudomonas other than the strain *Pseudomonas aeruginosa* mutant $SGRR_2$; and the microbial combination of:

(a) a microorganism of the strain *Pseudomonas aeruginosa* mutant $SGRR_2$; and (b) at least one of:
  (i) a microorganism of the genus Bacillus; and
  (ii) a microorganism of the genus Pseudomonas other than the strain *Pseudomonas aeruginosa* mutant $SGRR_2$.

16 Claims, No Drawings

MICROBIOLOGICAL PROCESS FOR REMOVING OLEAGINOUS MATERIAL FROM WASTEWATER AND MICROBIOLOGICAL COMBINATION CAPABLE OF SAME

BACKGROUND OF THE INVENTION

1. Field of the Invention

This invention relates to a process of removing oleaginous material from domestic, municipal and industrial wastewater and, more specifically, to a method for removing oleaginous material containing oleaginous material of animal origin from wastewater containing the same using a microbial combination of a novel mutant of *Pseudomonas aeruginosa* and at least one other microorganism of the genus Bacillus or of the genus Pseudomonas other than the novel mutant *Pseudomonas aeruginosa* whereby oleaginous material in the wastewater is degraded and thereby removed from the wastewater. Further, this invention relates to a novel microbial combination of the novel mutant of *Pseudomonas aeruginosa* in combination with at least one other microorganism of the genus Bacillus or of the genus Pseudomonas other than the novel mutant of *Pseudomonas aeruginosa*.

2. Description of the Prior Art

Fats and greases of either animal or vegetable origin, particularly of animal origin, have historically caused problems in systems for handling wastewater. Breakdown of these fats and greases is very slow, and due to their inherent nature of being water insoluble, fats and greases have a tendency to coat or completely clog drain or treatment systems. Disposal of fats is also hindered. Because they have a low specific gravity and a high melting point, fats float and solidify, causing difficulties in closed treatment systems such as in domestic septic tanks and in buried pipes where the grease and other waste become trapped and build up.

Further, problems arise in municipal and industrial systems due to the presence of grease and fats and, even in aerated waste handling lagoons and other systems as used by meat and poultry processors, the natural degradation process is often too slow, resulting in thick layers of grease and fat which build up to critical levels or carry through the system undigested.

As a result of the difficulty arising due to the inability of bacteria normally present in conventional treatment systems to degrade greases and fats at an acceptable rate, the treatment of wastewater containing such has been a problem in the past.

With the increasing concern as to minimization of the problems arising from pollution, biological processes utilizing microorganisms are being industrially municipally and domestically employed in an increasing amount, and a large amount of activity in research and development is occurring presently to develop new microbial strains capable of use in wastewater treatment both industrially, municipally and domestically. Even with this increased activity in investigating and developing strains of microorganisms to solve particular waste removal problems, a sufficiently acceptable solution to the problem of removing greases and fats which are present in wastewater from domestic, municipal and industrial sources has not yet been developed.

SUMMARY OF THE INVENTION

Accordingly, an object of this invention is to provide a method whereby oleaginous materials present in domestic, municipal and industrial wastewaters can be removed.

Another object of this invention is to provide a biological method for treatment of industrial, municipal and domestic wastewaters to not only remove biodegradable organic matter therefrom but to specifically reduce the level of or remove oleaginous materials therefrom.

A further object of this invention is to provide a biological treating process for removal of oleaginous materials from industrial, municipal and domestic waste waters using a novel mutant of *Pseudomonas aeruginosa*.

An even further object of this invention is to provide a biological treatment method for industrial, municipal and domestic wastewater to remove oleaginous materials therefrom and render such suitable for discharge into the biosphere, thereby minimizing problems of pollution.

A further object of this invention is to provide a treatment for industrial, municipal and domestic wastewaters whereby a combination of microorganisms acting synergistically with respect to oleaginous materials, particularly those which are of animal origin or which contain those of animal origin, is employed.

An additional object of this invention is to provide a novel combination of microorganisms which act synergistically to degrade oleaginous materials in industrial, municipal and domestic wastewaters.

In one embodiment of this invention, this invention provides a process for removing oleaginous material from wastewater comprising treating wastewater containing oleaginous material with a microbial combination of:

(a) a microorganism of the strain *Pseudomonas aeruginosa* mutant $SGRR_2$; and
(b) at least one of:
  (i) a microorganism of the genus Bacillus; and
  (ii) a microorganism of the genus Pseudomonas other than the strain *Pseudomonas aeruginosa* mutant $SGRR_2$.

In another embodiment of this invention, this invention provides a microbial combination synergistically acting with respect to degradation of oleaginous material, the microbial combination comprising:

(a) a microorganism of the strain *Pseudomonas aeruginosa* mutant $SGRR_2$; and
(b) at least one of:
  (i) a microorganism of the genus Bacillus; and
  (ii) a microorganism of the genus Pseudomonas other than the strain *Pseudomonas aeruginosa* mutant $SGRR_2$.

DETAILED DESCRIPTION OF THE INVENTION

The novel mutant of the species *Pseudomonas aeruginosa* $SGRR_2$ was produced by mutation of a parent strain of *Pseudomonas aeruginosa* designated *Pseudomonas aeruginosa* HCP (hereinafter "parent strain") isolated from the soil in Salem, Virginia.

This *Pseudomas aeruginosa* $SGRR_2$ (hereinafter "mutant strain") has been found, when used in combination with microorganisms of the genus Bacillus and microorganisms of the genus Pseudomonas other than this mutant strain, to be capable of degrading oleaginous materials and has the characteristics described below.

Pseudomonas aeruginosa SGRR₂

The cells of the mutant strain are gram-negative rods. The cells are motile and in culture, the cells are straight, not curved rods where less than about 1% of the cells exist in the form of long filaments of greater than five cell-units long. On Kings Medium A (described in E. O. King et al., *J. Lab. & Clin. Med.*, Volume 44, No. 2, page 303 (1954), and on Difco BACTO-Antibiotic Medium No. 3 (trade name produced by Difco Laboratories), a blue-green pyocyanin pigment is formed which diffuses into the surrounding medium. A characteristic grape-like odor is given off by cultures of *Pseudomonas aeruginosa* mutant SGRR₂ on both complex media, such as nutrient broth and nutrient agar, and on minimal salts-based media containing a carbon source, such as glucose. The mutant strain is incapable of utilizing acetate as a sole carbon source.

The mutant strain is an obligate aerobe, except in the presence of nitrate. On metabolism in the presence of nitrate, the strain produces nitrate reductase.

The cells of the mutant strain are incapable of accumulating poly-$\beta$-hydroxybutyric acid granules even though DL-hydroxybutyrate serves as a sole carbon source.

A preferred growth temperature range is about 20°–41° C., with optimal growth occurring at 37° C. No growth is observed in ten days at 14° C. The mutant strain is capable of growth on a glucose-containing minimal salts medium containing ammonium ion as the nitrogen source. The mutant strain has either only a small or absent requirement for trace metals because it is capable of growth in medium lacking magnesium, manganese, zinc, cobalt and iron which has been made with distilled deionized water. Thus the mutant strain does not appear to require any growth factor or vitamin supplement. The strain displays arginine dihydrolase activity and is capable of gelatin hydrolysis.

Pseudomonas aeruginosa HCP

The parent strain *Pseudomonas aeruginosa* HCP is a gram-negative, non-spore-forming rod. The cells are straight rods which have a single-polar flagellum, and the cells are motile. In culture, approximately 1% of the cells exist in the form of long filaments of greater than five cell units long. On Kings Medium A and on Difco BACTO-Antibiotic Medium 3, solidified with agar at temperatures from 20°–40° C., a blue-green diffusible pigment is formed. A characteristic grape-like odor is given off by cultures of *Pseudomonas aeruginosa* HCP on both complex media, such as nutrient broth and nutrient agar, and on minimal salts-based media containing a carbon source, such as glucose.

The parent strain *Pseudomonas aeruginosa* HCP is capable of growing on either a glucose or acetate containing minimal salts medium (Roy Curtiss, III, *J. Bact.*, 89, 28–40 (1965)) containing ammonium ion as a nitrogen source, thus demonstrating the strain does not appear to require any growth factor or vitamin supplement.

The parent strain is an obligate aerobe, although growth is possible anaerobically in the presence of nitrate, in which case a gas is formed. On metabolism in the presence of nitrate, the parent strain produces nitrate reductase.

The cells of the parent strain are incapable of accumulating poly-$\beta$-hydroxybutyric acid granules even though DL-hydroxybutyrate serves as a sole carbon source.

A preferred growth temperature range is about 20°–41° C., with optimal growth occurring at 37° C. No growth is observed in ten days at 14° C. The strain displays arginine dihydrolase activity and is capable of gelatin hydrolysis.

Other cultural characteristics and colonial morphology or these two *Pseudomonas aeruginosa* strains are shown in Tables 1–6 below.

In the following tables, *Pseudomonas aeruginosa* strain PAO (ATCC 13525) was employed as a known type strain for characterization purposes.

TABLE 1

MICROSCOPIC MORPHOLOGY

| CHARACTERISTIC | PSEUDOMONAS AERUGINOSA** | HCP | SGRR₂ |
|---|---|---|---|
| Cell Size* | | | |
| Length | 1.5–3.0 | 1.5–3.0 | 1.5–3.0 |
| Width | 0.5–0.8 | 0.5–0.8 | 0.5–0.8 |
| Gram Reaction | Negative rod | Negative rod | Negative rod |

*Wet mounts of ten-hour cultures (late exponential phase) viewed under phase contrast (1000X). Sizes given in micrometers.
**Data from Bergey's Manual of Determinative Bacteriology. 8th Ed., The Williams & Wilkins Co., Baltimore (1974).

TABLE 2

COLONIAL CHARACTERISTICS OF
*PSEUDOMONAS AERUGINOSA* HCP AND SGRR₂
(After 48 Hours At 35° C.)

*Pseudomonas aeruginosa* - HCP

Plate Count Agar
  Colonies are circular, flat and have a rough surface. Their edge is undulate and they are 5–10 mm in diameter. They are transparent and white in color. No pigment is produced.
Nutrient Agar
  Colonies are slightly irregular, flat and have a wrinkled surface. Their edge is undulate and they are 4–7 mm in diameter. They are transparent and white in color. No pigment is produced.
Hektoen Enteric Agar
  Colonies are slightly irregular, slightly convex with a wrinkled surface. They have an undulate edge and they are from 4–6 mm in diameter. They are transparent and green in color. No pigment is produced.
Pseudosel Agar
  Circular, convex colonies are smooth and have an entire edge. They are slightly opaque, white and are 1–1.5 mm in diameter. A fluorescent green pigment is produced.
Trypticase Soy Agar
  Slightly irregular colonies are flat and have a wrinkled edge. Their edge is undulate. They are white in color and are 3–6 mm in diameter. They are slightly opaque. A fluorescent yellow pigment is produced.

*Pseudomonas aeruginosa* - SGGR₂

Plate Count Agar
  Colonies are slightly irregular, flat and have a rough surface. Their edge is undulate and they are transparent with an opaque center. They measure 3–5 mm in diameter. They are white and produce a diffusible blue green pigment.
Nutrient Agar
  Colonies are irregular, flat and have a wrinkled surface. They are transparent with an opaque center, are 4–5 mm in diameter and have an undulate edge. The colonies are white and produce a diffusable green pigment.
Hektoen Enteric Agar
  Slightly irregular colonies are slightly undulate, have a wrinkled surface and are transparent. They are 6–7 mm in diameter, have an undulate edge, are green in color, and produce no pigment.
Pseudosel Agar

TABLE 2-continued
COLONIAL CHARACTERISTICS OF PSEUDOMONAS AERUGINOSA HCP AND SGRR₂
(After 48 Hours At 35° C.)

Circular, flat colonies with a rough surface have an entire edge. They are 3–6 mm in diameter. They are transparent and colorless, and produce a diffusible blue pigment.
Trypticase Soy Agar
  Colonies are circular, flat, transparent, have an undulate edge and have a rough surface. They are 5–7 mm in diameter. They are white, and produce a fluorescent diffusible green pigment.

NOTE:
Plate Count Agar and Hektoen Enteric Agar are products of Difco Laboratories. Pseudosel Agar, Nutrient Agar and Trypticase Soy Agar are products of Baltimore Biological Laboratories.

TABLE 3
UTILIZATION OF CARBON-CONTAINING COMPOUNDS FOR GROWTH

| COMPOUND* | PSEUDOMONAS AERUGINOSA | HCP | SGRR₂ |
|---|---|---|---|
| Carbohydrates (& Sugar Derivatives) | | | |
| $\alpha$ - Cellulose | + | + | + |
| L - Arabinose | − | − | − |
| D - Ribose | − | − | − |
| D - Glucose | + | + | + |
| Sucrose | − | − | − |
| Trehalose | − | − | − |
| D - Cellobiose | − | − | − |
| Xylose | − | − | − |
| Organic Acids | | | |
| Acetate | + | + | − |
| Propionate | − | − | − |
| Butyrate | + | + | + |
| Isobutyrate | − | − | − |
| Valerate | − | − | − |
| Caproate | − | − | − |
| Heptanoate | − | − | − |
| Caprate | − | + | + |
| Stearate | + | + | − |
| Dicarboxylic Acids | | | |
| Maleate | + | + | + |
| Malonate | − | − | − |
| Succinate | − | − | − |
| Glutarate | − | − | − |
| Saccharate | − | − | − |
| Hydroxyacids | | | |
| L - Malate | − | − | − |
| DLβ - Hydroxybutyrate | − | + | + |
| DL - Lactate | − | − | − |
| DL - Glycerate | + | + | + |
| Miscellaneous Organic Acids | | | |
| Citrate | − | − | − |
| $\alpha$ - Ketoglutarate | − | − | − |
| Pyruvate | + | + | + |
| Polyhydric Alcohols And Glycols | | | |
| Mannitol | + | + | + |
| Glycerol | + | + | + |
| Propyleneglycol | − | + | + |
| m - Inositol | − | − | − |
| Sorbitol | − | − | − |
| Alcohols | | | |
| Ethanol | − | + | + |
| n - Propanol | + | − | − |
| n - Butanol | ± | + | + |
| Non-Nitrogenous Aromatic And Other Cyclic Compounds | | | |
| Benzoate | − | − | − |
| Aliphatic Amino Acids | | | |
| L$\alpha$ - Alanine | + | − | − |
| D$\alpha$ - Alanine | − | − | − |
| $\beta$ - Alanine | | + | + |
| L - Leucine | − | + | + |
| L - Aspartate | + | + | + |
| L - Glutamate | + | + | + |
| L - Lysine | + | − | + |
| DL - Arginine | | + | + |
| L - Valine | − | − | − |
| Glycine | − | − | − |
| Asparagine | + | + | + |
| Amino Acids And Related Compounds Containing A Ring Structure | | | |
| L - Histidine | + | − | + |
| L - Proline | − | + | + |
| L - Tyrosine | − | − | − |
| Miscellaneous Nitrogenous Compounds | | | |
| Betaine | + | + | + |
| Sarcosine | − | − | − |
| Acetamide | + | + | + |
| Glucosamine | − | − | − |
| Detergents* | | | |
| Igepal CO 520 (2000 mg/l) | ± | − | − |
| Igepal CO 610 (2000 mg/l) | ± | − | − |
| Igepal CO 660 (2000 mg/l) | ± | − | − |

*Compound added at 0.5% to minimal salts medium (Curtiss (1965)).
** + indicates growth greater than blank; − indicates growth less than that of blank; ± indicates growth approximately equal to blank or weak growth, after 7 days at 30° C.
***Trade name for a non-ionic nonylphenol-ethylene oxide condensate produced by GAF.

TABLE 4
UTILIZATION OF NITROGENOUS COMPOUNDS AS SOLE NITROGEN SOURCE

| COMPOUND* | PSEUDOMONAS AERUGINOSA | HCP | SGRR₂ |
|---|---|---|---|
| NH₄Cl | − | − | − |
| KNO₃ | − | − | − |
| L - Glutamate | + | + | + |
| L - Aspartate | − | − | − |
| L - Alanine | − | − | + |

*Compound added at 0.5 g/100 ml to minimal salts medium (Curtiss (1965) but without NH₄Cl and NH₄NO₃) consisting of 0.5 g of D-glucose/100 ml.
** + indicates growth greater than blank; − indicates growth less than that of blank; ± indicates growth approximately equal to blank or weak growth, after 7 days at 30° C.

TABLE 5
CULTURE GROWTH IN PRESENCE OF HEAVY METALS

| HEAVY METAL* | CONCENTRATION | PSEUDOMONAS AERUGINOSA | HCP | SGRR₂ |
|---|---|---|---|---|
| HgSO₄ | $2 \times 10^{-3}$M | − | − | − |
| | $10^{-3}$M | − | − | − |
| | $10^{-4}$M | − | − | + |
| | $10^{-5}$M | + | + | + |
| CdCl₂ | $2 \times 10^{-3}$M | − | − | − |
| | $10^{-3}$M | − | − | − |
| | $10^{-4}$M | + | − | + |
| | $10^{-5}$M | + | − | + |
| CoCl₂ | $2 \times 10^{-3}$M | − | − | + |
| | $10^{-3}$M | − | − | + |
| | $10^{-4}$M | + | + | + |
| | $10^{-5}$M | + | + | + |
| AgSO₄ | $2 \times 10^{-3}$M | − | − | − |

TABLE 5-continued
CULTURE GROWTH IN PRESENCE OF HEAVY METALS

| HEAVY METAL* | CONCEN- TRATION | STRAIN RESPONSE** | | |
|---|---|---|---|---|
| | | PSEUDOMONAS AERUGINOSA | HCP | SGRR$_2$ |
| | $10^{-3}$M | − | − | − |
| | $10^{-4}$M | − | − | − |
| | $10^{-5}$M | − | − | − |
| Na$_2$HAsO$_4$ | 2 × $10^{-3}$M | − | + | + |
| | $10^{-3}$M | − | + | + |
| $10^{-4}$M | + | + | + | |
| | $10^{-5}$M | + | + | + |

*Heavy metal added to D-glucose containing (0.5%) minimal salts medium (Curtiss (1965)).
**Growth response scored: + indicates growth (no inhibition); − indicates no growth (inhibition).

TABLE 6
RESISTANCE OF CULTURES TO ANTIBIOTICS

| ANTIBIOTIC | STRAIN RESPONSE | |
|---|---|---|
| | HCP | SGRR$_2$ |
| Ampicillin | R* | R |
| Carbenicillin | S | I |
| Cephalothin | R | R |
| Chloramphenicol | R | R |
| Coly-mycin | S | S |
| Gentamicin | S | S |
| Kanamycin | R | R |
| Mandol | R | R |
| Streptomycin | R | R |
| Tobramycin | S | S |
| Tetracycline | R | R |
| Amikacin | S | S |

*Growth response on Pfizer Antimicrobial Susceptibility Disks; Pfizer, Inc. scored: S = sensitive to antibiotic; R = resistant to antibiotic; and I = intermediate.

On the basis of the morphological, cultural and physiological characteristics set forth above, the mutant strain has been identified as a member of the species *Pseudomonas aeroginosa* and has been designated herein as *Pseudomonas aeruginosa* SGRR$_2$. A culture of the strain has been deposited in the American Type Culture Collection and has received an accession number, ATCC-31480.

Further, on the basis of the morphological, cultural and physiological characteristics set forth above, the parent strain from which the mutant strain was developed has been identified as a member of the species *Pseudomonas aeruginosa* and has been designated herein as *Pseudomonas aeruginosa* HCP. A culture of the strain has been deposited in the American Type Culture Collection and has received an accession number, ATCC-31479.

As indicated above, the parent strain HCP, from which the mutant strain, SGRR$_2$, was developed, was isolated and was then mutated in the following manner. The mutation was carried out in a bench-top biotower which basically was a trickling filter. The biotower comprised a reservoir for a liquid and a column containing Pall rings of a plastic resin, one end of which column was placed just above the liquid in the reservoir. A pump was submerged in the liquid reservoir for recycling liquid through a tube to the top of the column for dispersion of the liquid down through the Pall ring packing.

The biotower was first pre-conditioned by forming a slime layer of the HCP culture on the Pall rings using a 3-liter volume of deionized water containing 2% whey, 0.5% disodium phosphate and 0.1% (NH$_4$)$_2$SO$_4$ inoculated with the HCP culture. This was allowed to circulate over the tower for 2 days at room temperature (about 20°–30° C.) until a heavy slime layer formed on the rings. Then 200 ppm Santophen-1 (a chlorinated phenol-type disinfectant, trade name produced by Monsanto) was added along with sufficient nonyl phenol-type surface active agent (Igepal CO 660, trade name produced by GAF) to disperse the Santophen-1.

Recycling of the liquid through the biotower was allowed to proceed for another 2 days at which time 0.2% 8-azaguanine, as a strong chemical mutagent, was added. Recycling of the liquid through the biotower was continued for another 72 hours at which time the reservoir containing the 3 liters of liquid as described above was poured out. The column was then rinsed by recycling with fresh deionized water and again filled to the 3-liter level and 500 ppm of Santophen-1 added.

Three different colony types of microorganisms that grew through this were isolated after 48 hours and set aside, and one of these was designated *Pseudomonas aeruginosa* SGRR$_2$. As will be demonstrated in greater detail in the Examples given hereinafter, this mutant was tested against oleaginous materials and found to be substantially non-active against oleaginous materials in wastewater when used alone, as was the parent strain *Pseudomonas aeruginosa* HCP, but synergistically active in degrading oleaginous materials when used in combination with the parent strain. Further, it was found that when the SGRR$_2$ mutant strain was used in combination with microorganisms of the genus Bacillus, such as *Bacillus subtilis,* also substantially not active alone against oleaginous materials, the combination was synergistically active against oleaginous materials.

Thus, it has been found that when the mutant strain *Pseudomonas aeruginosa* SGRR$_2$, including variants thereof, is employed in combination with the parent strain, *Pseudomonas aeruginosa* HCP, including variants thereof, or with a bacterium of the genus Bacillus, an extremely high, synergistic activity on degradation of oleaginous materials in wastewater is found.

While not desiring to be bound, and while the reasons for this synergistic activity at the present time are not completely understood, it is surmised that the presence of the *Pseudomonas aeruginosa* SGRR$_2$ in combination with another microorganism of the genus Pseudomonas or with a microorganism of the genus Bacillus that the metabolic path in degrading oleaginous materials of one organism complements or supplements that of the other organism present in combination therewith, resulting in this high, unexpected synergistic activity.

The microbial combination of (a) the *Pseudomonas aeruginosa* SGRR$_2$ and (b) the other organism of the genus Bacillus or the genus Pseudomonas (other than *Pseudomonas aeruginosa* SGRR$_2$) can be employed in cell count proportions ranging from about 1:99 to about 99:1 of (a) to (b) to achieve the objects of this invention.

The microbial combination employed in this invention can be cultured in wastewater containing the oleaginous material either using a batch process, a semi-continuous process or a continuous process, and such a microorganism combination is cultured for a time sufficient to degrade the oleaginous materials present in the wastewater and remove them or break them down into components capable of being degraded by other organisms normally found in biological wastewater treatment systems.

The microbial combination of this invention can be employed in ion exchange resin treatment systems, in trickling filter systems, in activated sludge treatment systems, in outdoor lagoons or pools, etc. Basically, all that is necessary is for the microbial combination to be placed in a situation of contact with wastewater containing the oleaginous material. In order to degrade the oleaginous material present in the wastewater, the microbial combination can be cultured at conditions of about 15° C. to about 42° C., preferably about 20° C. to about 38° C. Desirably, the pH is maintained in a range of about 5.5 to about 8.5, preferably 6.5 to 8.0. Control of the pH can be by monitoring of the system and an addition of appropriate pH adjusting materials to achieve this pH range.

The culturing is conducted basically under aerobic conditions of a dissolved oxygen concentration of about 2 ppm or more, preferably about 5 ppm or more. These conditions can be simply achieved in any manner conventional in the art and appropriate to the treatment system design being employed. For example, air can be bubbled into the system, the system can be agitated, a trickling system can be employed, etc.

Normally, the wastewater to be subjected to the process of this invention will contain sufficient nitrogen and phosphorus for culturing without the need for any additional source of nitrogen or phosphorus being added. However, in the event the wastewater is deficient in these two components, suitable available nitrogen sources, such as ammonia or an ammonium salt, e.g., ammonium sulfate, can be added to achieve an available nitrogen content of at least about 10 ppm or more per 100 $BOD_5$. Similarly, phosphorus can be supplemented, if necessary, by addition of materials such as orthophosphates, e.g., sodium phosphate, to achieve a phosphorus level in the wastewater of about 1 ppm or more per 100 $BOD_5$. In general, the treatment is conducted for a sufficient time to achieve the reduction in oleaginous material content desired and, in general, about 3 hours to about 1 week or longer, although this will depend upon the temperature of culturing, the volume to be treated and other factors, has been found to be suitable.

In the above manner, difficultly degradable oleaginous materials, such as those of animal origin or those containing oleaginous materials of animal origin, as well as other organic compounds which might be present in such wastewater streams, can be advantageously treated to provide treated wastewater suitable for discharge after any additional conventional processing such as settling, chlorination, etc. into rivers and streams.

The microbial combination of this invention employed in the process of this invention has been found to be extremely advantageous in the treatment of wastewater containing oleaginous materials. The microbial combination employed in this invention is particularly advantageous since such is resistant to shock loads due to the presence of high levels of toxic materials, such as heavy metals, and organic solvents, such as aromatic and aliphatic solvents, pesticides, chlorinated compounds, disinfectants, phenolics, thiocyanates, etc., which would basically poison a conventional biological treatment system and disrupt the metabolic pathway of the conventional organisms utilized. The microbial combination of this invention is resistant to such shock loads, and based on information to date, it is believed that many industrial wastewater systems from a variety of different types of industrial installations can be treated using the microbial combination of this invention.

Suitable examples of other organisms of the genus Pseudomonas, other than the *Pseudomonas aeruginosa* $SGRR_2$ mutant strain, which can be employed in the combination of this invention include those of the alcaligenes group, such as *Pseudomonas alcaligenes*, and those of the fluorescent group, such as *Pseudomonas fluorescens, Pseudomonas putida*, and other *Pseudomonas aeruginosa* strains.

Additionally, suitable microorganisms of the genus Bacillus which can be employed in combination with the *Pseudomonas aeruginosa* $SGRR_2$ mutant strain in this invention include *Bacillus subtilis, Bacillus licheniformis, Bacillus cereus, Bacillus thuringiensis, Bacillus megaterium, Bacillus circulans, Bacillus coagulans, Bacillus brevis, Bacillus sphaericus, Bacillus fastidiosus*, etc.

As can be seen from an examination of the results set forth in the Examples below, the microbial combination of this invention utilized in the process of this invention results in the ability to obtain approximately a 75-fold increase over that obtained with the use of Bacillus strains alone, and approximately a 4-fold increase over the results obtained where the *Pseudomonas aeruginosa* $SGRR_2$ mutant strain is employed alone or where the parent *Pseudomonas aeruginosa* HCP, from which the mutant strain was developed, is used alone. This 75-fold and 4-fold increase in the use of the microbial combination of this invention is highly unexpected in view of the performance of these microorganisms separately and thus provides the ability to effectively degrade and remove oleaginous materials from wastewater, thereby providing a solution to a wastewater treatment problem presently existing.

The term oleaginous material as employed herein basically includes any material of an oily, fatty or greasy nature of animal origin or containing such of animal origin, with specific examples including oils, fats and greases, such as lard, beef tallow, butter, chicken fat, and other animal fats.

The following Examples are given to illustrate the present invention in greater detail but are given merely for the purposes of exemplification and are not to be construed as limiting the scope of the present invention. Unless otherwise indicated herein, all parts, percents, ratios and the like are by weight.

EXAMPLE 1

One gram of lard (commercially available under the trade name "Valleydale Lard," containing BHT, BHA and propyl gallate), as an oleaginous material of animal origin, was placed in 100 ml of a basic salt solution having the composition set forth below in cotton-stoppered 250 ml Erlenmeyer flasks.

| | Basic Salt Solution |
|---|---|
| $NH_4Cl$ | 5 g/l |
| $Na_2SO_4$ | 2 g/l |
| $KH_2PO_3$ | 3 g/l |
| $MgSO_4$* | 1 g/l |
| $NH_4NO_3$ | 1 g/l |
| $K_2HPO_4$ | 9 g/l |

*Added after sterilization and cooling.

The flasks were sterilized, cooled and inoculated with one loop full of each of the microorganisms set forth below, and the flasks and contents were shaken for 5 days on a rotary shaker.

The results were analyzed by comparing flasks containing the microorganisms with an uninoculated control flask prepared and treated in the same manner as described above. The analysis was of the oil and grease amount present using a gravametric determination of the dried residue remaining after extraction of each flask, with 1,1,2-trichloro-1,2,2-trifluoroethane (based on *Standard Methods for the Examination of Waters and Wastewaters*, 14th Ed., page 513, Water Pollution Control Federation (1975)).

The results set forth in Table 7 below were obtained.

TABLE 7

| CULTURE | OIL & GREASE AMOUNT (GRAMS) | % REDUCTION* |
|---|---|---|
| Control (none) | 0.9732 | — |
| Comparison Bacillus Microorganism Combination | 0.9637 | 0.97 |
| *Pseudomonas aeruginosa* HCP | 0.7907 | 18.75 |
| *Pseudomonas aeruginosa* SGRR$_2$ | 0.8279 | 14.93 |
| *Pseudomonas aeruginosa* SGRR$_2$ + *Pseudomonas aeruginosa* HCP | 0.3186 | 67.26 |
| *Pseudomonas aeruginosa* SGRR$_2$ + Comparison Bacillus Microorganism Combination | 0.2390 | 75.44 |

*% Reduction is based on control flask.
Comparison Bacillus Microorganism Combination comprised an equal mixture by volume of *Bacillus subtilis* (strain producing mainly protease), *Bacillus subtilis* (strain producing mainly amylase), *Bacillus cereus* and *Bacillus circulans* (strain producing mainly cellulase).

COMPARISON EXAMPLE

The procedures described in Example 1 were repeated on a vegetable oil (commercially available under the trade name "Kroger Pure Vegetable Oil", a partially saturated soybean oil with oxystearin added and BHT, BHA and methyl silicone), as an oleaginous material of vegetable origin, to demonstrate the advantageous results obtained in this invention in degrading oleaginous material of animal origin or containing those of animal origin.

The results obtained are set forth in Table 8 below.

TABLE 8

| CULTURE | OIL & GREASE AMOUNT (GRAMS) | % REDUCTION* |
|---|---|---|
| Control (none) | 0.9887 | — |
| Comparison Bacillus Microorganism Combination | 0.5998 | 39.33 |
| *Pseudomonas aeruginosa* HCP | 0.0697 | 92.95 |
| *Pseudomonas aeruginosa* SGRR$_2$ | 0.1739 | 82.41 |
| *Pseudomonas aeruginosa* SGRR$_2$ + *Pseudomonas aeruginosa* HCP | 0.0610 | 93.31 |
| *Pseudomonas aeruginosa* SGRR$_2$ + Comparison Bacillus Microorganism Combination | 0.2640 | 73.29 |

*% Reduction is based on control flask.
Comparison Bacillus Microorganism Combination comprised an equal mixture by volume of *Bacillus subtilis* (strain producing mainly protease), *Bacillus subtilis* (strain producing mainly amylase), *Bacillus cereus* and *Bacillus circulans* (strain producing mainly cellulase).

EXAMPLE 2

In order to further demonstrate the synergistic effect obtained with the microbial combination of this invention in utilization of such in combination with other microorganisms outside the scope of this invention, the following procedures were conducted.

Caprate, a known fatty acid component of oleaginous materials, was employed, and degradation thereof in an agar-based substrate was evaluated. The degradation of the caprate in the agar base is exhibited by a clearing of the agar around the microorganism colony growth. Thus, a clear zone around a disk inoculated with a microorganism and placed on the caprate-containing agar base is formed, and by comparing the sizes of such zones made by various microorganisms or combinations thereof, the effectiveness of the microorganisms in degrading caprate can be thereby determined.

The procedures followed in this comparison involved suspending 24-hour cultures of each of the microorganisms set forth in Table 9 below in sterile physiological saline. All cultures, after suspension, had approximately equal optical densities. The suspensions of the microorganisms were mixed in the concentrations set forth in Table 9 below and absorbed on a paper disk of sterile filter paper having a diameter of 13 mm. The disks were then placed on the agar base containing 0.5% caprate plus minimal salts (Curtiss (1965)), and after 72 hours of incubation at 35° C., the zones of clearing were measured.

The results set forth in Table 9 below were obtained.

TABLE 9

| PERCENT OF CULTURE IN COMBINATION | | | ZONE OF |
|---|---|---|---|
| HCP | SGRR$_2$ | CBMC | CLEARING (mm) |
| 1 | 99 | — | 21 |
| 10 | 90 | — | 22 |
| 30 | 70 | — | 21.5 |
| 60 | 40 | — | 22 |
| 90 | 10 | — | 21 |
| 99 | 1 | — | 20 |
| 0.5 | 0.5 | 99 | 19.5 |
| 5 | 5 | 90 | 24 |
| 15 | 15 | 70 | 23.5 |
| 30 | 30 | 40 | 25 |
| 45 | 45 | 10 | 20 |
| 49.5 | 49.5 | 1 | 21 |
| — | 1 | 99 | 21.5 |
| — | 10 | 90 | 24 |
| — | 30 | 70 | 23.75 |
| — | 60 | 40 | 22.5 |
| — | 90 | 10 | 20.5 |
| — | 99 | 1 | 21 |
| 1 | — | 99 | 21 |
| 10 | — | 90 | 22 |
| 30 | — | 70 | 22 |
| 60 | — | 40 | 22.5 |
| 90 | — | 10 | 23.25 |
| 99 | — | 1 | 23.5 |

| PERCENT OF CULTURE IN COMBINATION | | | | | ZONE OF |
|---|---|---|---|---|---|
| HCP + SGRR$_2$* | BSP | BSA | BC | BCC | CLEARING (mm) |
| — | 100 | — | — | — | 0 |
| — | — | 100 | — | — | 0 |
| — | — | — | 100 | — | 0 |
| — | — | — | — | 100 | 0 |
| 50 | 50 | — | — | — | 22 |
| 50 | — | 50 | — | — | 22 |
| 50 | — | — | 50 | — | 21.25 |
| 50 | — | — | — | 50 | 22.75 |
| 33 | 33 | 33 | — | — | 22.75 |

TABLE 9-continued

| | | | | | |
|---|---|---|---|---|---|
| 33 | 33 | — | 33 | — | 23 |
| 33 | 33 | — | — | 33 | 21.5 |
| 33 | — | 33 | 33 | — | 19.5 |
| 33 | — | 33 | — | 33 | 21.5 |
| 33 | — | — | 33 | 33 | 23 |
| 25 | 25 | 25 | 25 | — | 21.5 |
| 25 | 25 | 25 | — | 25 | 22 |
| 25 | 25 | — | 25 | 25 | 20.25 |
| 25 | — | 25 | 25 | 25 | 22 |
| 25 | 25 | 25 | 25 | 25 | 19 |

*50% by volume each of HCP and SGRR$_2$.
NOTE:
Zone of clearing measured in millimeters, and result presented is an average of two different diameter measurements of the zone.
HCP = Pseudomonas aeruginosa HCP.
SGRR$_2$ = Pseudomonas aeruginosa SGRR$_2$.
BSP = Bacillus subtilis (strain mainly producing protease).
BSA = Bacillus subtilis (strain mainly producing amylase).
BC = Bacillus cereus.
BCC = Bacillus circulans (strain mainly producing amylase).
CBMC = Comparison Bacillus Microorganism Combination.

EXAMPLE 3

In this evaluation of the microbial combination of this invention, the waste treatment system of a large poultry processing plant through which 75,000 chickens were processed per day was employed. The wastewater treatment system comprised nine aerated lagoons of which the pH of the wastewater was monitored and adjusted to a pH of 6.5–7.5 by addition of bicarbonate as needed.

In this evaluation, a microorganism combination in dry form comprising 25% *Pseudomonas aeruginosa* HCP, 20% *Pseudomonas aeruginosa* SGRR$_2$, 20% of another *Pseudomonas aeruginosa* of substantially no activity against oleaginous materials and 25% of an equal mixture of *Bacillus subtilis* (strain mainly producing protease), *Bacillus subtilis* (strain mainly producing amylase), *Bacillus cereus* and *Bacillus circulans* (strain mainly producing cellulase), along with 10% unidentified microorganisms was employed.

Effluent wastewater was passed through the treatment system in an amount of 500,000 gallons per day, and the dry microorganism combination was placed in the first lagoon for wash through into the subsequent lagoons in the system. The dry microorganism culture was added in the following amounts:

50 pounds per day for 2 days
25 pounds per day for 3 days
10 pounds per day for 7 days
5 pounds per day for 7 days
3 pounds per day for each day thereafter During the test, the dissolved oxygen content, due to the aeration, was maintained above 2 ppm.

Samples were periodically obtained from the fourth lagoon and analyzed for chemical oxygen demand, biological oxygen demand, suspended solids and the presence of oil and grease, with the results set forth in Table 10 below being obtained. The day 0 results represent a 3-month average of the treatment system characteristics prior to the evaluation.

TABLE 10

| | EVALUATION | | | |
|---|---|---|---|---|
| DAY | COD | BOD | SUSPENDED SOLIDS | OIL & GREASE |
| 0 | 2620 | 260 | 401 | 104 |
| 8 | 1600 | 132 | 485 | 20 |
| 15 | 680 | 105 | 368 | 31 |
| 18 | 450 | 109 | 330 | 18 |
| 21 | 460 | 120 | 346 | 34 |

It was also found that no salmonella was present in the treated wastewater and the level of fecal coliforms was considerably reduced, the presence of these organisms previously being a problem.

While the invention has been described in detail and with respect to specific embodiments thereof, it will be apparent to one skilled in the art that various changes and modifications can be made therein without departing from the spirit and scope thereof.

What is claimed is:

1. A process for removing oleaginous materials of animal origin or containing such of animal origin from wastewater comprising treating, under aerobic conditions, wastewater containing said oleaginous material with a microbial combination of:
   (a) a microorganism of the strain *Pseudomonas aeruginosa* SGRR$_2$ (ATCC-31480); and
   (b) at least one of:
      (i) a microorganism of the genus Bacillus; and
      (ii) a microorganism of the genus Pseudomonas other than said strain *Pseudomonas aeruginosa* SGRR$_2$.

2. The process of claim 1, wherein said microorganism of the genus Bacillus is *Bacillus subtilis*, *Bacillus licheniformis*, *Bacillus cereus*, *Bacillus thuringiensis*, *Bacillus megaterium*, *Bacillus circulans*, *Bacillus coagulans*, *Bacillus brevis*, *Bacillus sphaericus* or *Bacillus fastidiosus*.

3. The process of claim 1, wherein said microorganism of the genus Bacillus is *Bacillus subtilis*, *Bacillus cereus* or *Bacillus circulans*.

4. The process of claim 1, wherein said microorganism of the genus Bacillus is *Bacillus subtilis*.

5. The process of claim 1, wherein said microorganism of the genus Pseudomonas is *Pseudomonas aeruginosa* HCP (ATCC-31479), *Pseudomonas aeruginosa* other than said *Pseudomonas aeruginosa* HCP, *Pseudomonas alcaligenes* or *Pseudomonas putida*.

6. The process of claim 1, wherein said microorganism of the genus Pseudomonas is *Pseudomonas aeruginosa* HCP (ATCC-31479).

7. The process of claim 1, wherein the cell count population proportion of said microorganism (a) to said microorganism (b) ranges from 1:99 to 99:1.

8. The process of claim 1, wherein said treating is under aerobic conditions at a temperature of about 15° C. to about 42° C. at a pH of about 6.5 to about 8.5 and at a dissolved oxygen concentration of about 2 ppm or more.

9. The process of claim 1, wherein said microbial combination comprises (a) said microorganism of the strain *Pseudomonas aeruginosa* SGRR$_2$, (b) (i) a microorganism of the genus Bacillus and (b) (ii) a microorganism of the genus Pseudomonas other than said strain *Pseudomonas aeruginosa* SGRR$_2$.

10. A microbial synergist combination comprising:
   (a) a biologically pure culture of a microorganism of the strain *Pseudomonas aeruginosa* SGRR$_2$ (ATCC-31480); and
   (b) at least one of:
      (i) a microorganism of the genus Bacillus; and (ii) a microorganism of the genus Pseudomonas other than said strain *Pseudomonas aeruginosa* SGRR$_2$, said combination of microorganisms (a) and (b) synergistically acting to utilize oleaginous materials of animal origin or containing the same as a source of assimilable carbon and degrade said oleaginous materials of animal origin or containing the same.

11. The combination of claim 10, wherein said microorganism of the genus Bacillus is *Bacillus subtilis, Bacillus licheniformis, Bacillus cereus, Bacillus thuringiensis, Bacillus megaterium, Bacillus circulans, Bacillus coagulans, Bacillus brevis, Bacillus sphaericus* or *Bacillus fastidiosus.*

12. The combination of claim 10, wherein said microorganism of the genus Bacillus is *Bacillus subtilis, Bacillus cereus* or *Bacillus circulans.*

13. The combination of claim 10, wherein said microorganism of the genus Bacillus is *Bacillus subtilis.*

14. The combination of claim 10, wherein said microorganism of the genus Pseudomonas is *Pseudomonas aeruginosa* HCP (ATCC-31479), *Pseudomonas aeruginosa* other than said *Pseudomonas aeruginosa* HCP, *Pseudomonas alcaligenes* or *Pseudomonas putida.*

15. The combination of claim 10, wherein said microorganism of the genus Pseudomonas is *Pseudomonas aeruginosa* HCP (ATCC-31479).

16. A biologically pure culture of a microorganism of the strain *Pseudomonas aeruginosa* SGRR$_2$ (ATCC-31480) capable of utilizing oleaginous materials of animal origin or containing same as an assimilable source of carbon.

* * * * *